(12) United States Patent
Aristizabal et al.

(10) Patent No.: US 9,132,025 B2
(45) Date of Patent: Sep. 15, 2015

(54) BIFURCATED ENDOVASCULAR PROSTHESIS HAVING TETHERED CONTRALATERAL LEG

(71) Applicant: TriVascular, Inc., Santa Rosa, CA (US)

(72) Inventors: Diego Aristizabal, Santa Rosa, CA (US); Michael V. Chobotov, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 199 days.

(21) Appl. No.: 13/803,067

(22) Filed: Mar. 14, 2013

(65) Prior Publication Data

US 2013/0338760 A1 Dec. 19, 2013

Related U.S. Application Data

(60) Provisional application No. 61/660,105, filed on Jun. 15, 2012.

(51) Int. Cl.
| | |
|---|---|
| *A61F 2/06* | (2013.01) |
| *A61F 2/954* | (2013.01) |
| *A61F 2/07* | (2013.01) |
| *A61F 2/95* | (2013.01) |

(52) U.S. Cl.
CPC . *A61F 2/954* (2013.01); *A61F 2/07* (2013.01); *A61F 2002/065* (2013.01); *A61F 2002/9511* (2013.01); *A61F 2250/0003* (2013.01); *A61F 2250/0071* (2013.01)

(58) Field of Classification Search
CPC ....... A61F 2/06; A61F 2/07; A61F 2002/823; A61F 2002/9511; A61B 5/6851
USPC ........... 623/1.11–1.16, 1.23–1.25, 1.35, 1.36; 606/198, 194, 108, 191, 192, 195
See application file for complete search history.

(56) References Cited

U.S. PATENT DOCUMENTS

| | | |
|---|---|---|
| 5,489,295 A | 2/1996 | Piplani et al. |
| 5,609,625 A | 3/1997 | Piplani et al. |
| 5,628,783 A | 5/1997 | Quiachon et al. |
| 5,639,278 A | 6/1997 | Dereume et al. |
| 5,662,675 A | 9/1997 | Polanskyj Stockert et al. |
| 5,676,696 A | 10/1997 | Marcade |

(Continued)

FOREIGN PATENT DOCUMENTS

| | | |
|---|---|---|
| EP | 2111828 A2 | 10/2009 |
| WO | 00/69367 A1 | 11/2000 |
| WO | 2013/151924 A1 | 10/2013 |

OTHER PUBLICATIONS

International Search Report and Written Opinion dated Nov. 6, 2013 for corresponding PCT application.

*Primary Examiner* — Todd Manahan
*Assistant Examiner* — Erich Herbermann
(74) *Attorney, Agent, or Firm* — Hoffmann & Baron, LLP

(57) ABSTRACT

An endovascular delivery system includes a bifurcated and inflatable prosthesis including a main tubular body having an open end and opposed ipsilateral and contralateral legs defining a graft wall therein between. A tether is disposed securably disposed to the contralateral leg, and the contralateral leg is releasably restrained towards the ipsilateral leg tether to prevent undesirable movement of the contralateral leg. A release wire within the endovascular delivery system releasably retains the tether near the ipsilateral leg.

21 Claims, 12 Drawing Sheets

(56) References Cited

U.S. PATENT DOCUMENTS

| | | |
|---|---|---|
| 5,683,449 A | 11/1997 | Marcade |
| 5,693,088 A | 12/1997 | Lazarus |
| 5,749,920 A | 5/1998 | Quiachon et al. |
| 5,769,885 A | 6/1998 | Quiachon et al. |
| 5,782,909 A | 7/1998 | Quiachon et al. |
| 5,800,518 A | 9/1998 | Piplani et al. |
| 5,824,039 A | 10/1998 | Piplani et al. |
| 5,824,044 A | 10/1998 | Quiachon et al. |
| 5,855,598 A | 1/1999 | Pinchuk |
| 5,860,998 A | 1/1999 | Robinson et al. |
| 5,871,536 A | 2/1999 | Lazarus |
| 5,904,713 A | 5/1999 | Leschinsky |
| 5,944,750 A | 8/1999 | Tanner et al. |
| 5,957,940 A | 9/1999 | Tanner et al. |
| 5,957,973 A | 9/1999 | Quiachon et al. |
| 5,993,481 A | 11/1999 | Marcade et al. |
| 5,997,556 A | 12/1999 | Tanner |
| 6,039,758 A | 3/2000 | Quiachon et al. |
| 6,132,459 A | 10/2000 | Piplani et al. |
| 6,162,246 A | 12/2000 | Barone |
| 6,165,214 A | 12/2000 | Lazarus |
| 6,183,481 B1 | 2/2001 | Lee et al. |
| 6,197,046 B1 | 3/2001 | Piplani et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,235,050 B1 | 5/2001 | Quiachon et al. |
| 6,241,759 B1 | 6/2001 | Piplani et al. |
| 6,248,118 B1 | 6/2001 | Tanner et al. |
| 6,270,516 B1 | 8/2001 | Tanner et al. |
| 6,306,164 B1 | 10/2001 | Kujawski |
| 6,322,587 B1 | 11/2001 | Quiachon et al. |
| 6,355,061 B1 | 3/2002 | Quiachon et al. |
| 6,371,919 B1 | 4/2002 | Tanner et al. |
| 6,395,022 B1 | 5/2002 | Piplani et al. |
| 6,409,750 B1 | 6/2002 | Hyodoh et al. |
| 6,409,757 B1 | 6/2002 | Trout, III et al. |
| 6,416,542 B1 | 7/2002 | Marcade et al. |
| 6,464,721 B1 | 10/2002 | Marcade et al. |
| 6,520,974 B2 | 2/2003 | Tanner et al. |
| 6,540,778 B1 | 4/2003 | Quiachon et al. |
| 6,592,615 B1 | 7/2003 | Marcade et al. |
| 6,635,066 B2 | 10/2003 | Tanner et al. |
| 6,660,033 B1 | 12/2003 | Marcade et al. |
| 6,663,666 B1 | 12/2003 | Quiachon et al. |
| 6,669,718 B2 | 12/2003 | Besselink |
| 6,676,694 B1 | 1/2004 | Weiss |
| 6,682,537 B2 * | 1/2004 | Ouriel et al. ......... 606/108 |
| 6,682,557 B1 | 1/2004 | Quiachon et al. |
| 6,695,875 B2 | 2/2004 | Stelter et al. |
| 6,761,733 B2 | 7/2004 | Chobotov et al. |
| 6,767,361 B2 | 7/2004 | Quiachon et al. |
| 6,802,859 B1 | 10/2004 | Pazienza et al. |
| 6,808,534 B1 | 10/2004 | Escano |
| 6,878,164 B2 | 4/2005 | Kujawski et al. |
| 6,964,679 B1 | 11/2005 | Marcade et al. |
| 6,984,244 B2 | 1/2006 | Perez et al. |
| 7,029,496 B2 | 4/2006 | Rakos et al. |
| 7,118,594 B2 | 10/2006 | Quiachon et al. |
| 7,195,639 B2 | 3/2007 | Quiachon et al. |
| 7,235,083 B1 | 6/2007 | Perez et al. |
| 7,235,095 B2 | 6/2007 | Haverkost et al. |
| 7,294,147 B2 | 11/2007 | Hartley |
| 7,435,253 B1 | 10/2008 | Hartley et al. |
| 7,452,371 B2 | 11/2008 | Pavcnik et al. |
| 7,520,894 B2 | 4/2009 | Pavcnik et al. |
| 7,527,645 B2 | 5/2009 | Perez et al. |
| 7,597,710 B2 | 10/2009 | Obermiller |
| 7,604,661 B2 | 10/2009 | Pavcnik et al. |
| 7,628,803 B2 | 12/2009 | Pavcnik et al. |
| 7,803,574 B2 | 9/2010 | Desai et al. |
| 7,918,882 B2 | 4/2011 | Pavcnik et al. |
| 7,972,616 B2 | 7/2011 | Dubrow et al. |
| 8,118,862 B2 | 2/2012 | Saeed |
| 8,128,680 B2 | 3/2012 | Arnault De La Menardiere et al. |
| 8,128,686 B2 | 3/2012 | Paul, Jr. et al. |
| 2001/0016748 A1 | 8/2001 | Tanner et al. |
| 2001/0037142 A1 | 11/2001 | Stelter et al. |
| 2001/0039450 A1 | 11/2001 | Pavcnik et al. |
| 2002/0007193 A1 | 1/2002 | Tanner et al. |
| 2002/0013620 A1 | 1/2002 | Kujawski |
| 2002/0026214 A1 | 2/2002 | Tanner et al. |
| 2002/0077692 A1 | 6/2002 | Besselink |
| 2002/0151953 A1 | 10/2002 | Chobotov et al. |
| 2003/0004560 A1 | 1/2003 | Chobotov et al. |
| 2003/0088306 A1 | 5/2003 | Rakos et al. |
| 2003/0158597 A1 | 8/2003 | Quiachon et al. |
| 2003/0163188 A1 | 8/2003 | Haverkost et al. |
| 2003/0167087 A1 | 9/2003 | Piplani et al. |
| 2003/0176912 A1 | 9/2003 | Chuter et al. |
| 2004/0002714 A1 | 1/2004 | Weiss |
| 2004/0054401 A1 | 3/2004 | Kujawski et al. |
| 2004/0082990 A1 | 4/2004 | Hartley |
| 2004/0117004 A1 | 6/2004 | Osborne et al. |
| 2004/0138734 A1 | 7/2004 | Chobotov et al. |
| 2004/0153143 A1 | 8/2004 | Quiachon et al. |
| 2004/0186558 A1 | 9/2004 | Pavcnik et al. |
| 2004/0193252 A1 | 9/2004 | Perez et al. |
| 2004/0210301 A1 | 10/2004 | Obermiller |
| 2004/0213766 A1 | 10/2004 | Francois |
| 2004/0243221 A1 | 12/2004 | Fawzi et al. |
| 2005/0015141 A1 | 1/2005 | Quiachon et al. |
| 2005/0038498 A1 | 2/2005 | Dubrow et al. |
| 2005/0043785 A1 | 2/2005 | Tanner et al. |
| 2005/0084514 A1 | 4/2005 | Shebuski et al. |
| 2005/0143807 A1 | 6/2005 | Pavcnik et al. |
| 2005/0177224 A1 | 8/2005 | Fogarty et al. |
| 2005/0187613 A1 | 8/2005 | Bolduc et al. |
| 2005/0221072 A1 | 10/2005 | Dubrow et al. |
| 2005/0228484 A1 | 10/2005 | Stephens et al. |
| 2006/0009833 A1 | 1/2006 | Chobotov et al. |
| 2006/0015176 A1 | 1/2006 | White et al. |
| 2006/0020326 A9 | 1/2006 | Bolduc et al. |
| 2006/0036314 A1 | 2/2006 | Perez et al. |
| 2006/0111770 A1 | 5/2006 | Pavcnik et al. |
| 2006/0142846 A1 | 6/2006 | Pavcnik et al. |
| 2006/0155358 A1 | 7/2006 | LaDuca et al. |
| 2006/0155363 A1 | 7/2006 | LaDuca et al. |
| 2006/0161245 A1 | 7/2006 | Rakos et al. |
| 2006/0204738 A1 | 9/2006 | Dubrow et al. |
| 2006/0286063 A1 | 12/2006 | Shebuski et al. |
| 2007/0010875 A1 | 1/2007 | Trout et al. |
| 2007/0050015 A1 | 3/2007 | O'Brien et al. |
| 2007/0150051 A1 | 6/2007 | Arnault De La Menardiere et al. |
| 2007/0156228 A1 | 7/2007 | Majercak et al. |
| 2007/0167955 A1 | 7/2007 | Arnault De La Menardiere et al. |
| 2007/0225797 A1 | 9/2007 | Krivoruhko |
| 2007/0282247 A1 | 12/2007 | Desai et al. |
| 2007/0299498 A1 | 12/2007 | Perez et al. |
| 2008/0039362 A1 | 2/2008 | Shebuski et al. |
| 2008/0039926 A1 | 2/2008 | Majercak et al. |
| 2008/0097586 A1 | 4/2008 | Pavcnik et al. |
| 2008/0103587 A1 | 5/2008 | Henderson et al. |
| 2008/0183274 A1 | 7/2008 | LaDuca et al. |
| 2008/0208309 A1 | 8/2008 | Saeed |
| 2008/0221668 A1 | 9/2008 | Pinchuk et al. |
| 2008/0255656 A1 | 10/2008 | Saeed |
| 2008/0275542 A1 | 11/2008 | LaDuca et al. |
| 2008/0288045 A1 | 11/2008 | Saeed |
| 2009/0005847 A1 | 1/2009 | Adams |
| 2009/0043373 A1 | 2/2009 | Arnault De La Menardiere et al. |
| 2009/0048662 A1 | 2/2009 | Pavcnik et al. |
| 2009/0099649 A1 | 4/2009 | Chobotov et al. |
| 2009/0125095 A1 | 5/2009 | Bui et al. |
| 2009/0132026 A1 | 5/2009 | Martin et al. |
| 2009/0138067 A1 | 5/2009 | Pinchuk et al. |
| 2009/0157169 A1 | 6/2009 | Pavcnik et al. |
| 2009/0162643 A1 | 6/2009 | Dubrow et al. |
| 2009/0182405 A1 | 7/2009 | Arnault De La Menardiere et al. |
| 2009/0202621 A1 | 8/2009 | Maldonado et al. |
| 2009/0259296 A1 | 10/2009 | Mciff et al. |
| 2009/0264991 A1 | 10/2009 | Paul, Jr. et al. |
| 2009/0299455 A1 | 12/2009 | Sutermeister et al. |
| 2009/0299462 A1 | 12/2009 | Fawzi et al. |

(56) References Cited

U.S. PATENT DOCUMENTS

| | | |
|---|---|---|
| 2009/0301182 A1 | 12/2009 | Nikanorov |
| 2009/0319029 A1 | 12/2009 | Evans et al. |
| 2010/0057191 A1 | 3/2010 | Pavcnik et al. |
| 2010/0161028 A1 | 6/2010 | Chuter et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0298923 A1 | 11/2010 | Sutermeister et al. |
| 2010/0324589 A1 | 12/2010 | Carpenter et al. |
| 2011/0201984 A1 | 8/2011 | Dubrow et al. |
| 2012/0012569 A1 | 1/2012 | Severino |
| 2012/0022636 A1 | 1/2012 | Chobotov |
| 2012/0029608 A1 | 2/2012 | Chobotov |

\* cited by examiner

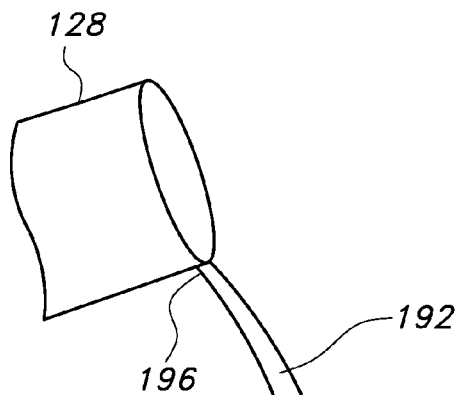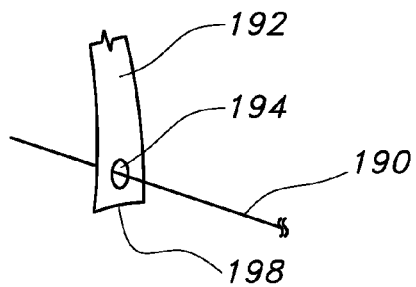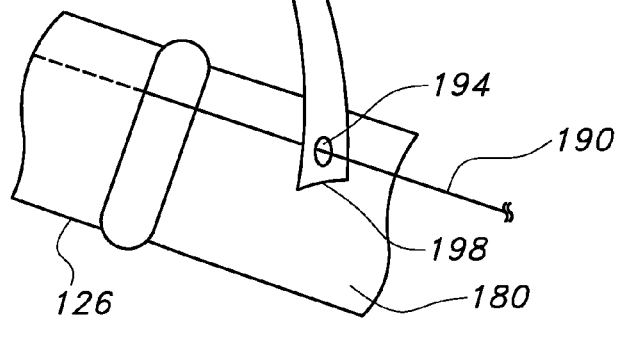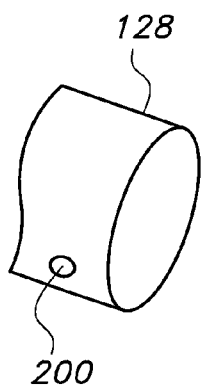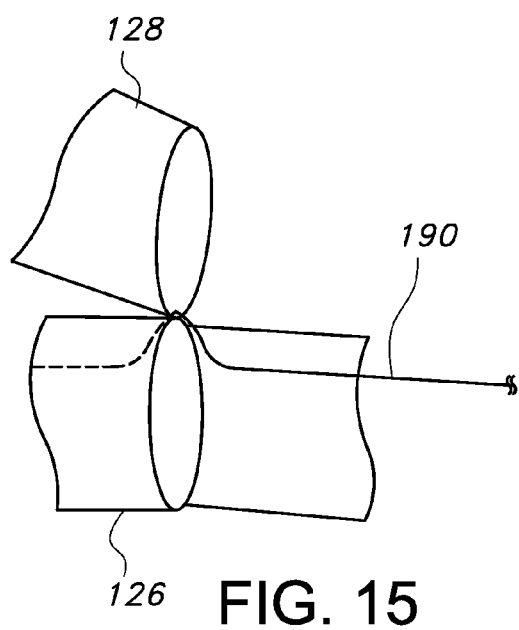
FIG. 13
FIG. 14
FIG. 15
FIG. 16

BIFURCATED ENDOVASCULAR PROSTHESIS HAVING TETHERED CONTRALATERAL LEG

CROSS-REFERENCE TO RELATED APPLICATIONS

This application claims the benefit of U.S. Provisional Application No. 61/660,105, filed Jun. 15, 2012, the contents of which are incorporated by reference herein.

FIELD OF THE INVENTION

The present invention is related to an endovascular delivery system for an endovascular prosthesis. More particularly, the present invention is related to an endovascular delivery system having a bifurcated and inflatable prosthesis having a tether from a contralateral leg to restrain movement of the contralateral leg with respect to an ipsilateral leg of the prosthesis.

BACKGROUND OF THE INVENTION

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W.B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant™ and Talent™ Abdominal Stent Grafts sold by Medtronic, Inc. of Minneapolis, Minn.; the Zenith Flex® AAA Endovascular Graft and the Zenith TX2® TAA Endovascular Graft, both sold by Cook Medical, Inc. of Bloomington, Ind.; the AFX™ Endovascular AAA system sold by Endologix, Inc. of Irvine, Calif.; and the Gore® Excluder® AAA Endoprosthesis sold by W.L. Gore & Associates, Inc. of Flagstaff, Ariz. A commercially available stent graft for the treatment of TAAs is the Gore® TAG® Thoracic Endoprosthesis sold by W.L. Gore & Associates, Inc. of Flagstaff, Ariz.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated. What have been needed are stent graft systems, delivery systems and methods that are adaptable to a wide range of patient anatomies and that can be safely and reliably deployed using a flexible low profile system.

SUMMARY OF THE INVENTION

In one aspect of the present invention an endovascular delivery system includes a bifurcated and inflatable prosthesis including a main tubular body having an open end and opposed ipsilateral and contralateral legs defining a graft wall therein between, the ipsilateral and contralateral legs having open ends, and the main tubular body and the ipsilateral and contralateral legs having inflatable channels; the ipsilateral leg including an ipsilateral tab extending from the open end of the ipsilateral leg, the tab including at least two holes; an elongate guidewire having at least two outwardly projecting members, the outwardly projecting members being sized to at least partially fit within the at least one of the at least two holes of the ipsilateral tab; a release wire slidable disposed within the at least two outwardly projecting members of the elongate guidewire and within one of the at least two holes of the ipsilateral tab; and a tether having opposed contralateral and ipsilateral ends, the contralateral end of the tether being securably disposed at the open end of the contralateral leg, the ipsilateral end of the tether having a hole, the release wire being slidably disposed through the hole of the tether to so engage the tether; wherein withdrawal of the release wire releases the ipsilateral tab and the tether from the elongate guidewire. The elongate guidewire may be extendable through the ipsilateral leg and through the main tubular body.

When the release wire engages the tether, the open end of the contralateral leg is proximally disposed and restrained towards the open end of the ipsilateral leg. In such a restrained position, the contralateral leg is restricted from significant longitudinal movement so as to prevent bunching up of the contralateral leg and is also is restricted from significant rotational movement so as to prevent misalignment within a bodily lumen.

The endovascular delivery system may further include an elongate outer tubular sheath having an open lumen and opposed proximal and distal ends with a medial portion therein between, the proximal end of the outer tubular sheath securably disposed to a first handle; an elongate inner tubular member having a tubular wall with an open lumen and opposed proximal and distal ends with a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle; the elongate guidewire slidably disposed within the inner tubular member; the distal end of the outer tubular sheath being slidably disposed past and beyond the distal end of the inner tubular member to define a prosthesis delivery state and slidably retractable to the medial portion of the inner tubular member to define a prosthesis unsheathed state.

The prosthesis may include non-textile polymeric material; for example, polytetrafluoroethylene. In some embodiments, the polytetrafluoroethylene may be non-porous polytetrafluoroethylene. The prosthesis may further include a metallic expandable member securably disposed at or near the open end of the main tubular body of the prosthesis.

In another aspect of the present invention, a method for delivering a bifurcated prosthesis, includes providing a bifurcated and inflatable prosthesis including: a main tubular body having an open end and opposed ipsilateral and contralateral legs defining a graft wall therein between, the ipsilateral and contralateral legs having open ends, and the main tubular body and the ipsilateral and contralateral legs having inflatable channels; the ipsilateral leg including an ipsilateral tab extending from the open end of the ipsilateral leg, the tab including at least two holes; providing an elongate guidewire having at least two outwardly projecting members, the outwardly projecting members being sized to at least partially fit within at least one of the at least two holes of the ipsilateral tab; providing a release wire slidable disposed within the at least two outwardly projecting members of the elongate guidewire and within the at least two holes of the ipsilateral tab; providing a tether having opposed contralateral and ipsilateral ends, the contralateral end of the tether being securably disposed at the open end of the contralateral leg, the ipsilateral end of the tether having a hole, the release wire being slidably disposed through the hole of the tether to so engage the tether; and withdrawing the release wire to release the ipsilateral tab and the tether from the elongate guidewire.

When the release wire engages the tether, the open end of the contralateral leg is proximally disposed and restrained towards the open end of the ipsilateral leg and the contralateral leg is restricted from significant longitudinal movement so as to prevent bunching up of the contralateral leg. The contralateral leg is also restricted from significant rotational movement so as to prevent misalignment within a bodily lumen.

In some aspects of the present invention, the endovascular prosthesis may be a modular endovascular graft assembly including a bifurcated main graft member formed from a supple graft material having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. The network of inflatable channels may be disposed anywhere on the main graft member including the ipsilateral and contralateral legs. The network of inflatable channels may be configured to accept a hardenable fill or inflation material to provide structural rigidity to the main graft member when the network of inflatable channels is in an inflated state. The network of inflatable channels may also include at least one inflatable cuff disposed on a proximal portion of the main graft member which is configured to seal against an inside surface of a patient's vessel. The fill material can also have transient or chronic radiopacity to facilitate the placement of the modular limbs into the main graft member.

A proximal anchor member may be disposed at a proximal end of the main graft member and be secured to the main graft member. The proximal anchor member may have a self-expanding proximal stent portion secured to a self-expanding distal stent portion with struts having a cross sectional area that is substantially the same as or greater than a cross sectional area of proximal stent portions or distal stent portions adjacent the strut. At least one ipsilateral graft extension having a fluid flow lumen disposed therein may be deployed with the fluid flow lumen of the graft extension sealed to and in fluid communication with the fluid flow lumen of the ipsilateral leg of the main graft member. At least one contralateral graft extension having a fluid flow lumen disposed therein may be deployed with the fluid flow lumen of the graft extension sealed to and in fluid communication with the fluid flow lumen of the contralateral leg of the main graft member. For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm; more specifically, about 3 cm to about 5 cm.

In another aspect of the present invention, an endovascular prosthesis may include a bifurcated and inflatable prosthesis having a main tubular body having an open end and opposed ipsilateral and contralateral legs defining a graft wall therein between, where the ipsilateral and contralateral legs have open ends, and further where the main tubular body and the ipsilateral and contralateral legs have inflatable channels; and a web of biocompatible material disposed between the contralateral leg and the ipsilateral leg and secured to the contralateral leg and the ipsilateral leg. The inclusion of the web with the endovascular prosthesis may prevent, restrict or inhibit the contralateral leg from significant longitudinal movement so as to prevent bunching up of the contralateral leg during delivery of the endovascular prosthesis. The inclusion of the web with the endovascular prosthesis may also prevent, restrict or inhibit significant rotational movement of the contralateral leg during delivery so as to prevent misalignment within a bodily lumen. The web may be releasably secured to the contralateral leg and the ipsilateral leg.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE DRAWINGS

FIG. 13 is a schematic depiction of the ends of the contralateral and ipsilateral graft legs having a contralateral tether.

FIG. 14 is a schematic depiction of a release wire releasably engaging a portion of the tether of FIG. 13.

FIGS. 15 through 18 depict alternate embodiments of the present invention for restraining the contralateral leg.

DETAILED DESCRIPTION OF THE INVENTION

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms. With regard to graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
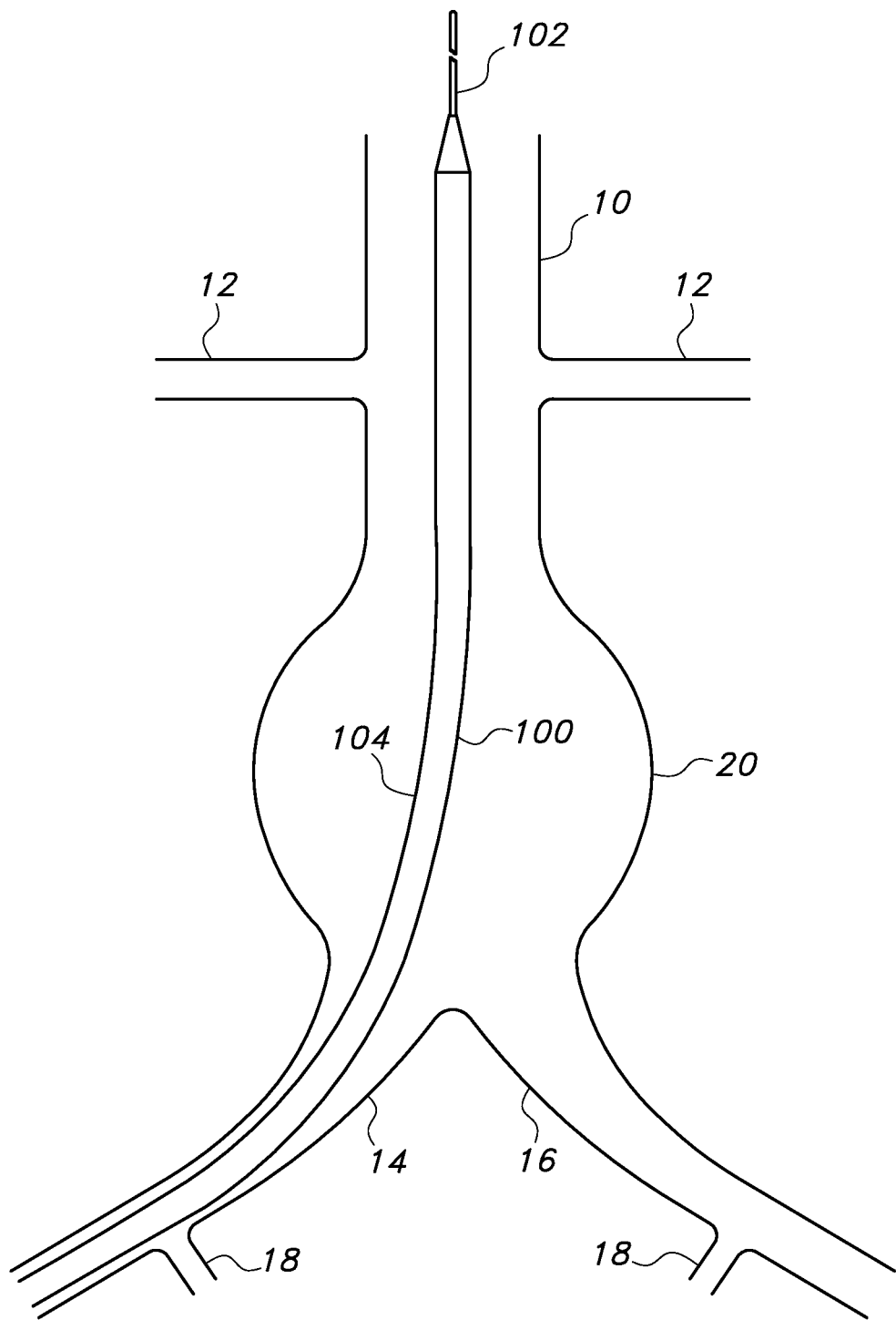
FIG. 1 depicts an initial deployment state of the endovascular delivery system of the present invention within a patient's vasculature.

FIG. 1 illustrates an embodiment of a deployment sequence of an embodiment of an endovascular prosthesis (not shown), such as a modular stent graft assembly. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to an inflatable stent-graft, may then be advanced over a guidewire through the delivery sheath and into the patient's vasculature.

FIG. 1 depicts the initial placement of the endovascular delivery system 100 of the present invention within a patient's vasculature. The endovascular delivery system 100 may be advanced along a guidewire 102 proximally upstream of blood flow into the vasculature of the patient including iliac arteries 14, 16 and aorta 10 shown in FIG. 1. While the iliac arties 14, 16 may be medically described as the right and left common iliac arteries, respectively, as used herein iliac artery 14 is described as an ipsilateral iliac artery and iliac artery 16 is described as a contralateral iliac artery. The flow of the patient's blood (not shown) is in a general downward direction in FIG. 1. Other vessels of the patient's vasculature shown in FIG. 1 include the renal arteries 12 and hypogastric arteries 18.

The endovascular delivery system 100 may be advanced into the aorta 10 of the patient until the endovascular prosthesis (not shown) is disposed substantially adjacent an aortic aneurysm 20 or other vascular defect to be treated. The portion of the endovascular delivery system 100 that is advance through bodily lumens is in some embodiments a low profile delivery system; for example, having an overall outer diameter of less than 14 French. Other diameters are also useful, such as but not limited to less than 12 French, less than 10 French, or any sizes from 10 to 14 French or greater. Once the endovascular delivery system 100 is so positioned, an outer sheath 104 of the endovascular delivery system 100 may be retracted distally so as to expose the prosthesis (not shown) which has been compressed and compacted to fit within the inner lumen of the outer sheath 104 of the endovascular delivery system 100.

Figure 2:
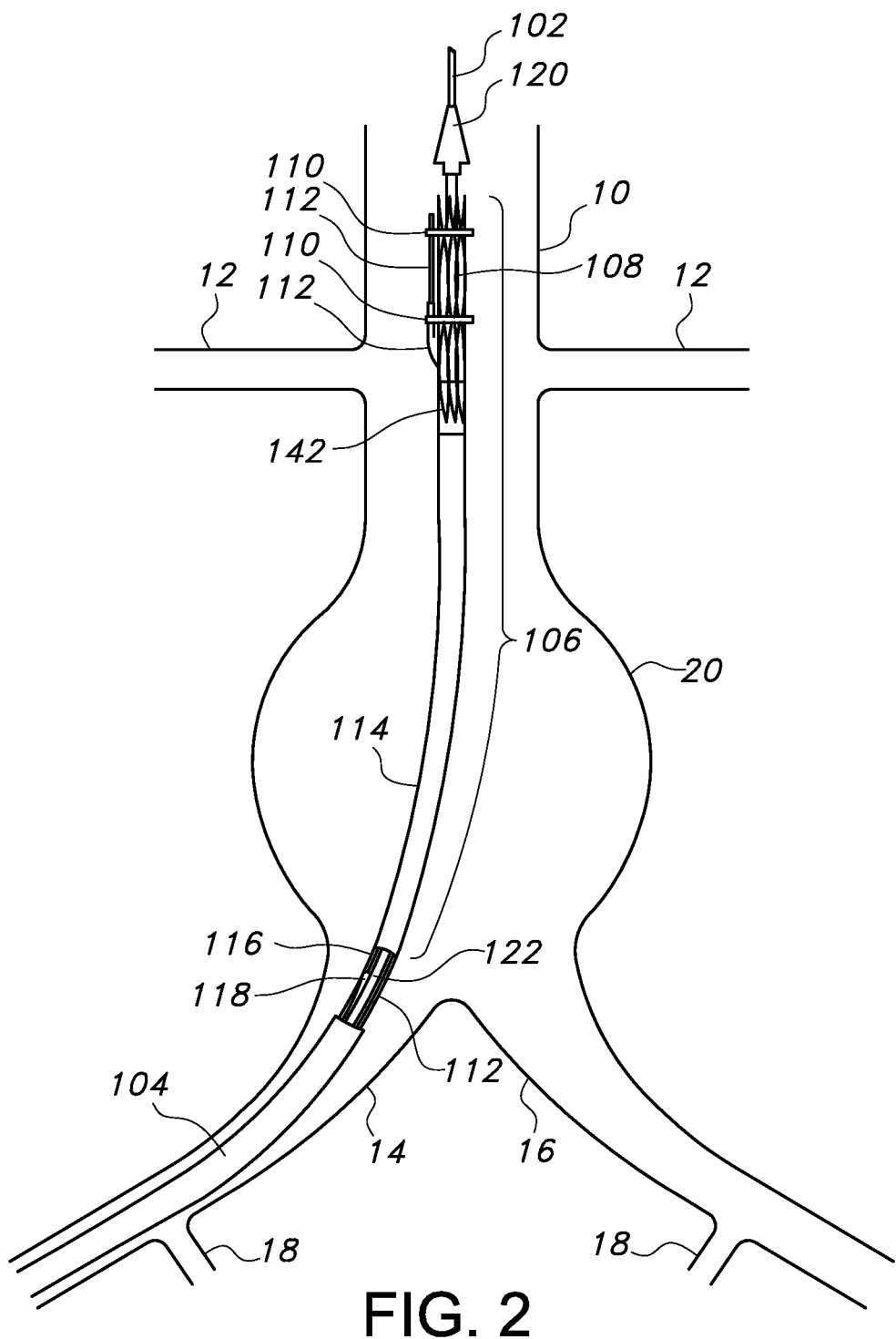
FIG. 2 depicts a deployment state of the endovascular delivery system of the present invention within a patient's vasculature after withdrawal of an outer sheath.

As depicted in FIG. 2, once the endovascular delivery system 100 is so positioned, the outer sheath 104 of the endovascular delivery system 100 may be retracted distally so as to expose the endovascular prosthesis 106 which has been compressed and compacted to fit within the inner lumen of the outer sheath 104 of the endovascular delivery system 100. The outer sheath 104 may be formed of a body compatible material. In some embodiments, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. In some embodiments, the biocompatible polymers include polypropylene (PP), polytetrafluoroethylene (PTFE), polyethylene terephthalate (PET), high density polyethylene (HDPE), combinations and copolymers thereof, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/ polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. In some embodiments, the outer sheath 104 may be made of polymeric materials, e.g., polyimides, polyester elastomers (Hytrel®), or polyether block amides (Pebax®), polytetrafluoroethylene, and other thermoplastics and polymers. The outside diameter of the outer sheath 104 may range from about 0.1 inch to about 0.4 inch. The wall thickness of the outer sheath 104 may range from about 0.002 inch to about 0.015 inch. The outer sheath 104 may also include an outer hydrophilic coating. Further, the outer sheath 104 may include an internal braided or otherwise reinforced portion of either metallic or polymeric filaments. In addition to being radially compressed when disposed within an inner lumen of the outer sheath 104 of the endovascular delivery system 100, a proximal stent 108 may be radially restrained by high strength flexible belts 110 in order to maintain a small profile and avoid engagement of the proximal stent 108 with a body lumen wall until deployment of the proximal stent 108 is initiated. The belts 110 can be made from any high strength, resilient material that can accommodate the tensile requirements of the belt members and remain flexible after being set in a constraining configuration. Typically, belts 110 are made from solid ribbon or wire of a shape memory alloy such as nickel titanium or the like, although other metallic or polymeric materials are possible. Belts 110 may also be made of braided metal filaments or braided or solid filaments of high strength synthetic fibers such as Dacron®, Spectra or the like. An outside transverse cross section of the belts 110 may range from about 0.002 to about 0.012 inch, specifically, about 0.004 to about 0.007 inch. The cross sections of belts 110 may generally take on any shape, including rectangular (in the case of a ribbon), circular, elliptical, square, etc. The ends of the belts 110 may be secured by one or more stent release wires or elongate rods 112 which extend through looped ends (not shown) of the belts 110. The stent release wires or elongate rods 112 may be disposed generally within the prosthesis 106 during delivery of the system 100 to the desired bodily location. For example, the stent release wires or elongate rods 112 may enter and exit the guidewire lumen 122 or other delivery system lumen as desired to affect controlled release of the stent 108, including if desired controlled and staged release of the stent 108. Once the outer sheath 104 of the endovascular delivery system 100 has been retracted, the endovascular delivery system 100 and the endovascular prosthesis 106 may be carefully positioned in an axial direction such that the proximal stent 108 is disposed substantially even with the renal arteries.

In some embodiments, the endovascular prosthesis 106 includes an inflatable graft 114. The inflatable graft may be a bifurcated graft having a main graft body 124, an ipsilateral graft leg 126 and a contralateral graft leg 128. The inflatable graft 114 may further include a fill port 116 in fluid communication with an inflation tube 118 of the endovascular delivery system 100 for providing an inflation medium (not shown). The distal portion of the endovascular delivery system 100 may include a nosecone 120 which provides an atraumatic distal portion of the endovascular delivery system 100. The guidewire 102 is slidably disposed within a guidewire lumen 122 of the endovascular delivery system 100.

Figure 3:
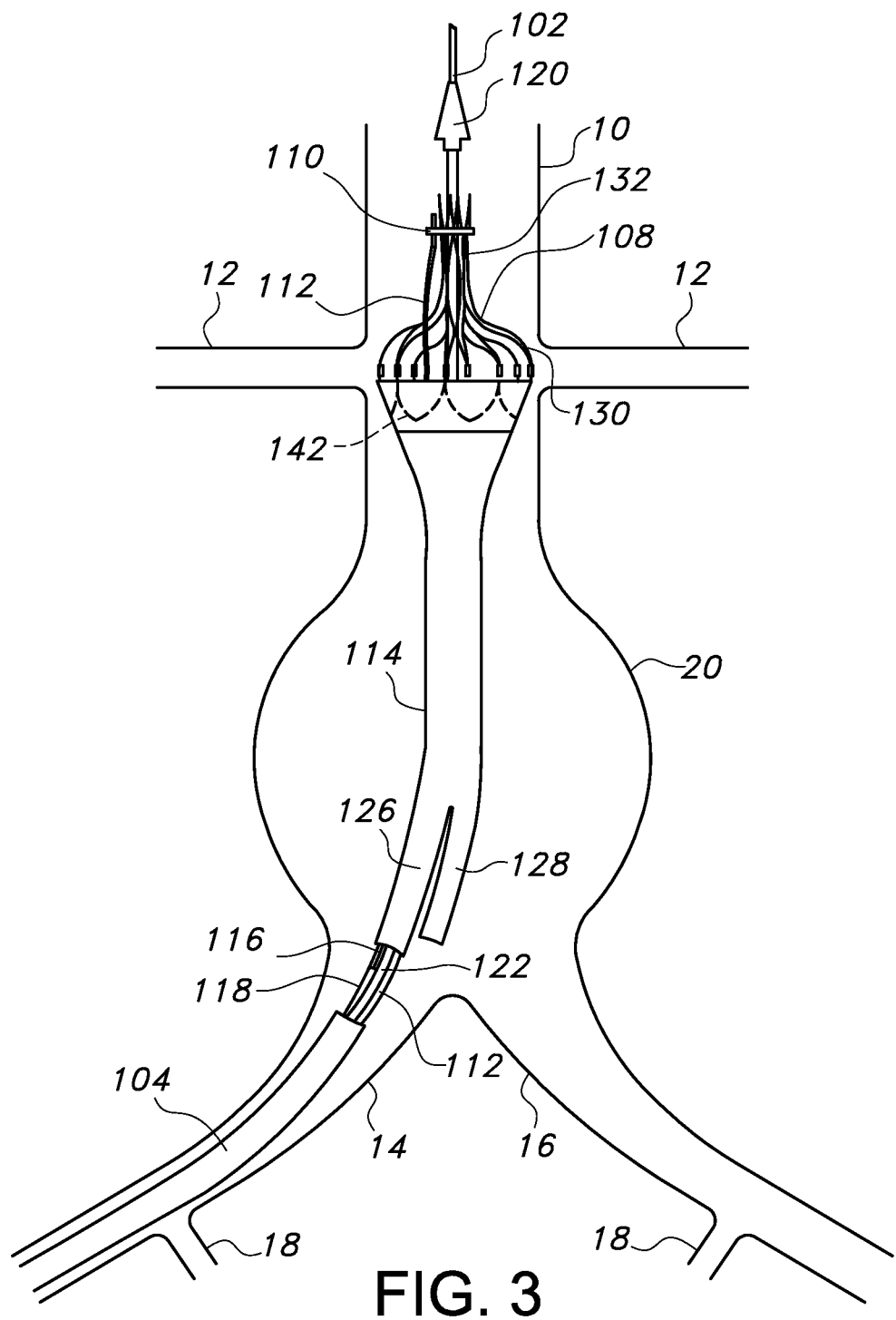
FIG. 3 depicts a deployment state of the endovascular delivery system of the present invention within a patient's vasculature after an initial and partial stent deployment.

As depicted in FIG. 3, deployment of the proximal stent 108 may begin with deployment of the distal portion 130 of stent 108 by retracting the stent release wire or rod 112 that couples ends of belt 110 restraining the distal portion 130 of the stent 108. The distal portion 130 of stent 108 may be disposed to the main graft body 124 via a connector ring 142. The stent 108 and/or the connector ring 142 may be made from or include any biocompatible material, including metallic materials, such as but not limited to, nitinol (nickel titanium), cobalt-based alloy such as Elgiloy, platinum, gold, stainless steel, titanium, tantalum, niobium, and combinations thereof. The present invention, however, is not limited to the use of such a connector ring 142 and other shaped connectors for securing the distal portion 130 of the stent 108 at or near the end of the main graft body 124 may suitably be used. Additional axial positioning typically may be carried out even after deploying the distal portion 130 of the stent 108 as the distal portion 130 may provide only partial outward radial contact or frictional force on the inner lumen of the patient's vessel or aorta 10 until the proximal portion 132 of the stent 108 is deployed. Once the belt 110 constraining the proximal portion 132 of the stent 108 has been released, the proximal portion 132 of the stent 108 self-expands in an outward radial direction until an outside surface of the proximal portion 132 of the stent 108 makes contact with and engages an inner surface of the patient's vessel 10.

Figure 4:
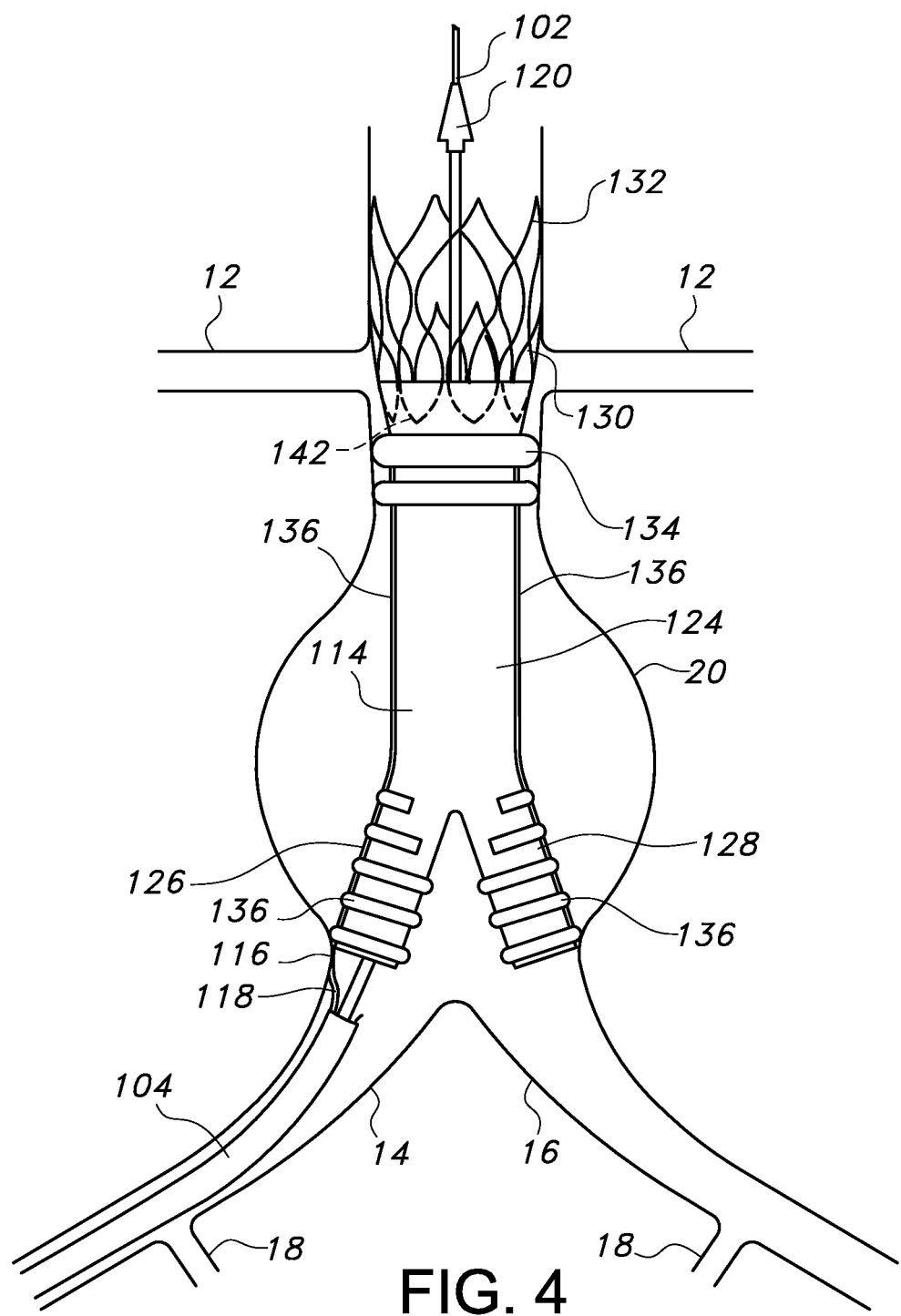
FIG. 4 depicts a deployment state of the endovascular delivery system of the present invention within a patient's vasculature after a stent deployment.

As depicted in FIG. 4, after the distal portion 130 of the stent 108 has been deployed, the proximal portion 132 of the stent 108 may then be deployed by retracting the wire 112 that couples the ends of the belt 110 restraining the proximal portion 132 of the stent 108. As the proximal portion 132 of the stent 108 self-expands in an outward radial direction, an outside surface of the proximal portion 132 of the stent 108 eventually makes contact with the inside surface of the patient's aorta 10. For embodiments that include tissue engaging barbs (not shown) on the proximal portion 132 of the stent 108, the barbs may also be oriented and pushed in a general outward direction so as to make contact and engage the inner surface tissue of the patient's vessel 10, which further secures the proximal stent 108 to the patient's vessel 10.

Once the proximal stent 108 has been partially or fully deployed, the proximal inflatable cuff 134 may then be filled through the inflation port 116 with inflation material injected through an inflation tube 118 of the endovascular delivery system 100 which may serve to seal an outside surface of the inflatable cuff 134 to the inside surface of the vessel 10. The remaining network of inflatable channels 136 may also be filled with pressurized inflation material at the same time which provides a more rigid frame like structure to the inflatable graft 114. For some embodiments, the inflation material may be a biocompatible, curable or hardenable material that may cured or hardened once the network of inflatable channels 136 are filled to a desired level of material or pressure within the network or after passage of a predetermined period of time. Some embodiments may also employ radiopaque inflation material to facilitate monitoring of the fill process and subsequent engagement of graft extensions (not shown). The material may be cured by any of the suitable methods discussed herein including time lapse, heat application, application of electromagnetic energy, ultrasonic energy application, chemical adding or mixing or the like. Some embodiments for the inflation material that may be used to provide outward pressure or a rigid structure from within the inflatable cuff 134 or network of inflatable channels 136 may include inflation materials formed from glycidyl ether and amine materials. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

The network of inflatable channels 136 may be partially or fully inflated by injection of a suitable inflation material into the main fill port 116 to provide rigidity to the network of inflatable channels 136 and the graft 114. In addition, a seal is produced between the inflatable cuff 134 and the inside surface of the abdominal aorta 10. Although it is desirable to partially or fully inflate the network of inflatable channels 136 of the graft 114 at this stage of the deployment process, such inflation step optionally may be accomplished at a later stage if necessary.

Figure 5:
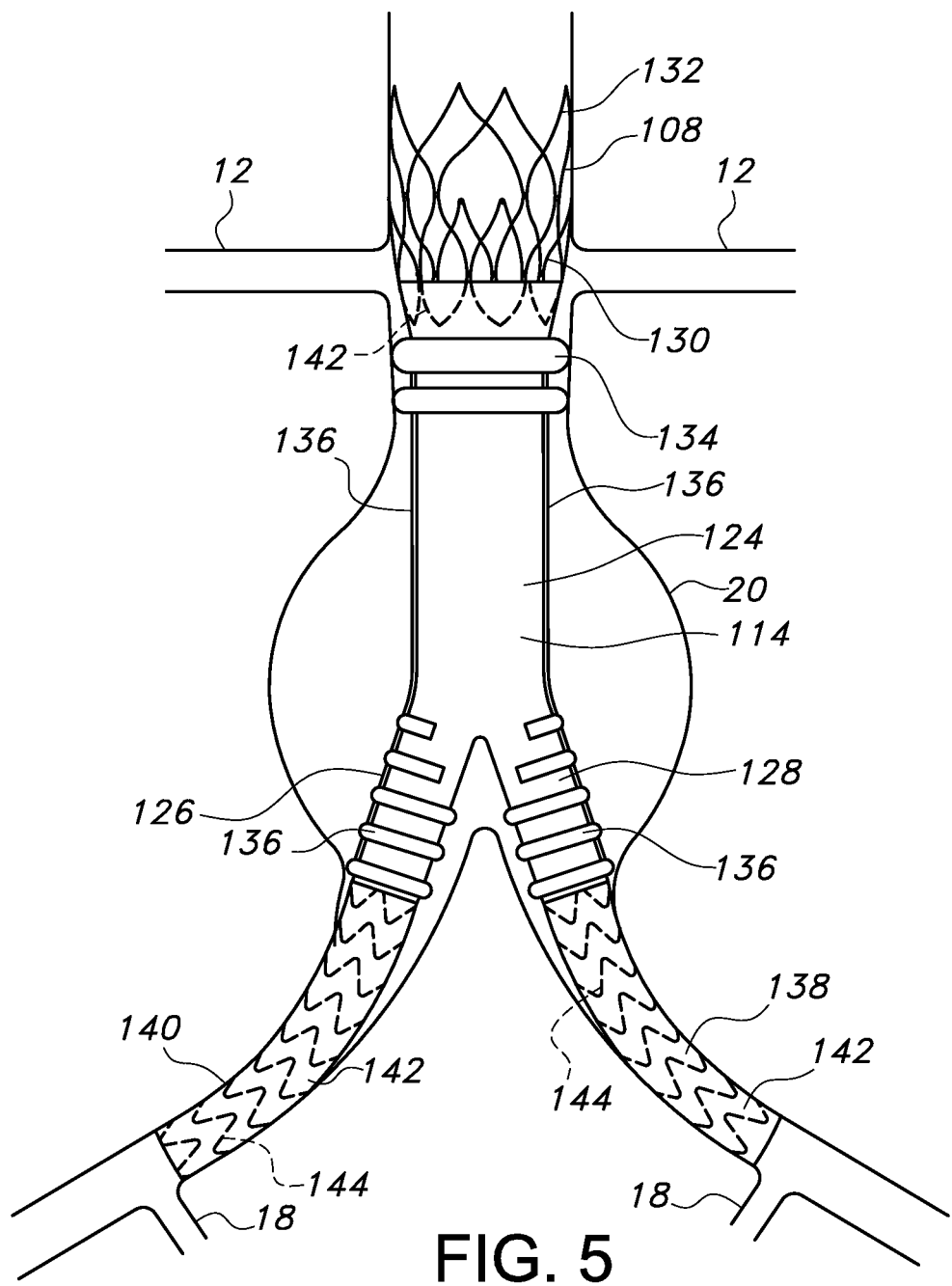
FIG. 5 depicts a deployed bifurcated endovascular prosthesis with graft leg extensions.

Once the graft 114 is deployed and the inflatable channels 136 thereof have been filled and expanded, another delivery catheter (not shown) may be used to deploy a contralateral graft extension 138, as depicted in FIG. 5. The contralateral graft extension 138 is in an axial position which overlaps the contralateral leg 128 of the graft 114. The amount of desired overlap of the graft extension 138 with the contralateral leg 128 may vary depending on a variety of factors including vessel morphology, degree of vascular disease, patient status and the like. However, for some embodiments, the amount of axial overlap between the contralateral graft extension 138 and the contralateral leg 128 may be about 1 cm to about 5 cm; more specifically, about 2 cm to about 4 cm. Once the contralateral graft extension 138 has been deployed, an ipsilateral graft extension 140 may be similarly deployed in the ipsilateral graft leg 126.

For some deployment embodiments, the patient's hypogastric arteries may be used to serve as a positioning reference point to ensure that the hypogastric arteries are not blocked by the deployment. Upon such a deployment, the distal end of a graft extension 138 or 140 may be deployed anywhere within a length of the ipsilateral leg 126 or contralateral leg 128 of the graft 114. Also, although only one graft extension 140, 138 is shown deployed on the ipsilateral side and contralateral side of the graft assembly 114, additional graft extensions 140, 138 may be deployed within the already deployed graft extensions 140, 138 in order to achieve a desired length extension of the ipsilateral leg 126 or contralateral leg 128. For some embodiments, about 1 to about 5 graft extensions 138, 140 may be deployed on either the ipsilateral or contralateral sides of the graft assembly 114. Successive graft extensions 138, 140 may be deployed within each other so as to longitudinally overlap fluid flow lumens of successive graft extensions.

Graft extensions 138, 140, which may be interchangeable for some embodiments, or any other suitable extension devices or portions of the main graft section 124 may include a variety of suitable configurations. For some embodiments, graft extensions 138, 140 may include a polytetrafluoroethylene (PTFE) graft 142 with helical nitinol stent 144.

Further details of the endovascular prosthesis 106 and/or graft extensions 138, 140 may be found in commonly owned U.S. Pat. Nos. 6,395,019; 7,081,129; 7,147,660; 7,147,661; 7,150,758; 7,615,071; 7,766,954 and 8,167,927 and commonly owned U.S. Published Application No. 2009/0099649, the contents of all of which are incorporated herein by reference in their entirety. Details for the manufacture of the endovascular prosthesis 106 may be found in commonly owned U.S. Pat. Nos. 6,776,604; 7,090,693; 7,125,464; 7,147,455; 7,678,217 and 7,682,475, the contents of all of which are incorporated herein by reference in their entirety. Useful inflation materials for the inflatable graft 114 may be found in may be found in commonly owned U.S. Published Application No. 2005/0158272 and 2006/0222596, the contents of all of which are incorporated herein by reference in their entirety. Additional details of an endovascular delivery system having an improved radiopaque marker system for accurate prosthesis delivery may be found in commonly owned U.S. Provisional Application No. 61/660,413, entitled "Endovascular Delivery System With An Improved Radiopaque Marker Scheme", filed Jun. 15, 2012, the contents of which are incorporated the herein by reference in their entirety.

Useful graft materials for the endovascular prosthesis 106 include, but are not limited, polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. In some embodiments, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernable node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. Such PTFE layers may lack distinct, parallel fibrils that interconnect adjacent nodes of ePTFE, typically have no discernable node and fibril microstructure when viewed at a magnification of up to 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Number is determined by measuring the time necessary for a given volume of air, typically, 25 cc, 100 cc or 300 cc, to flow through a standard 1 square inch of material or film under a standard pressure, such as 12.4 cm column of water. Such testing may be carried out with a Gurley Densometer, made by Gurley Precision Instruments, Troy, N.Y. Details of such useful PTFE materials and methods for manufacture of the same may be found in commonly owned U.S. Patent Application Publication No. 2006/0233991, the contents of which are incorporated herein by reference in their entirety.

Figure 6:
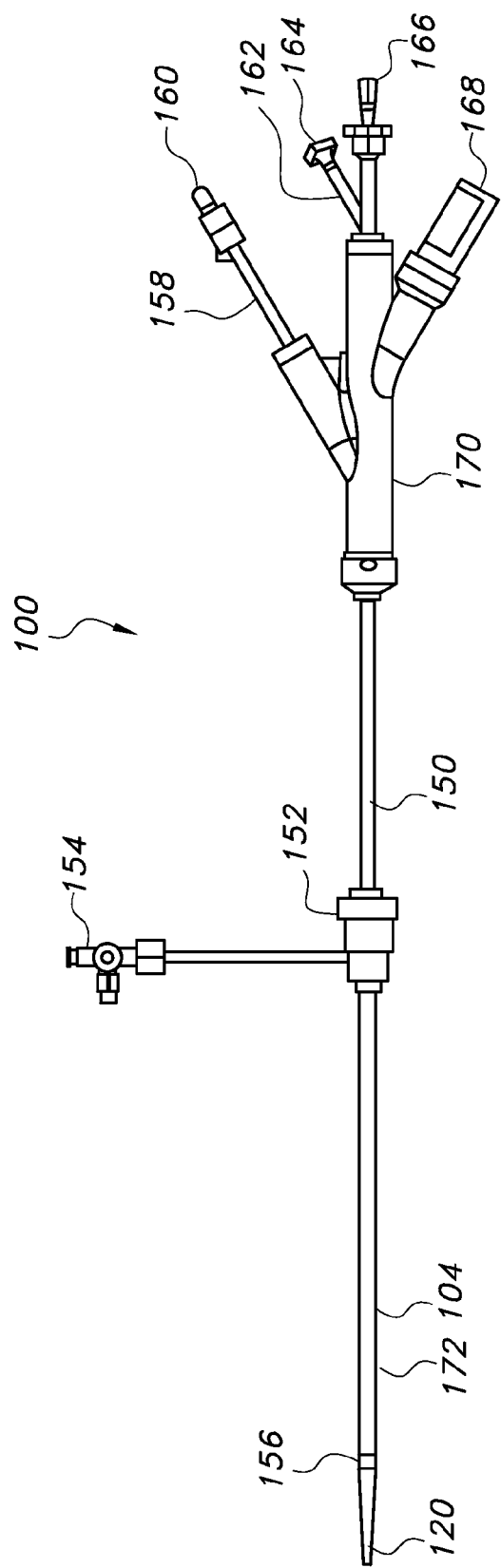
FIG. 6 is a side elevational view of the endovascular delivery system of the present invention.

FIG. 6 is a side elevational view of the endovascular delivery system 100 of the present invention. The endovascular delivery system 100 may include, among other things, the nosecone 120; the outer sheath 104; a retraction knob or handle 152 for the outer sheath 104; a flush port 154 for the outer sheath 104; an outer sheath radiopaque marker band 156; an inner tubular member or hypotube 150; an inflation material or polymer fill connector port 158; an inflation material or polymer fill cap 160; a guidewire flush port 162; a guidewire flush port cap 164; a guidewire port 166; and nested stent release knobs 168; interrelated as shown. The inner tubular member 150 may be formed from any of the above-described materials for the outer sheath 104. In addition, a portion of the inner tubular member 150 or even the entire inner tubular member 150 may be in the form of a metallic hypotube. Details of useful metallic hypotubes and endovascular delivery systems containing the same may be found in commonly owned U.S. Provisional Application No. 61/660,103, entitled "Endovascular Delivery System With Flexible And Torqueable Hypotube", the contents of which are incorporated herein by reference in their entirety.

The flush port 154 for the outer sheath 104 may be used to flush the outer sheath 104 during delivery stages. The outer sheath 104 may have a radiopaque marker band to aid the practitioner in properly navigating the delivery system 100 to the desired bodily site. The outer sheath 104 is retractable by movement of the retraction knob or handle 152 for the outer sheath 104 by a practitioner towards the proximal handle assembly 170 of the delivery system 100. The inner tubular member or hypotube 150 is disposed from the inner tubular member or hypotube 150 toward a proximal portion of the delivery system 100. The inflation material or polymer fill connector port 158 and the inflation material or polymer fill cap 160 are useful for providing inflation material (e.g., polymeric fill material) to inflate proximal inflatable cuffs 134 and the network of inflatable channels 136 of the inflatable graft 114. The guidewire flush port 162 and the guidewire flush port cap 164 are useful for flushing the guidewire port 166 during delivery stages of the delivery system 100. The nested stent release knobs 168 contains a series of nested knobs (not shown) that that are used to engage release mechanisms for delivery of the endovascular prosthesis 106. Further details, including but not limited to methods, catheters and systems, for deployment of endovascular prostheses are disclosed in commonly owned U.S. Pat. Nos. 6,761,733 and 6,733,521 and commonly owned U.S. Patent Application Publication Nos. 2006/0009833 and 2009/0099649, all of which are incorporated by reference herein in their entirety.

Figure 7:
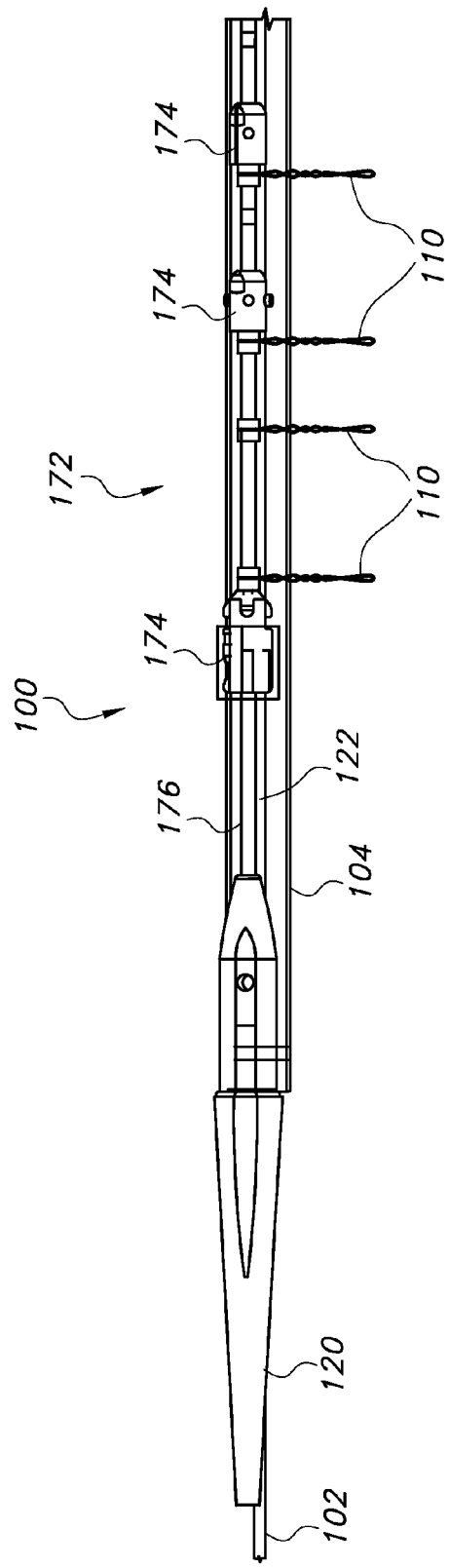
FIG. 7 is a side elevational and partial cutaway view of the distal portion of the endovascular delivery system of the present invention.
Figure 8:
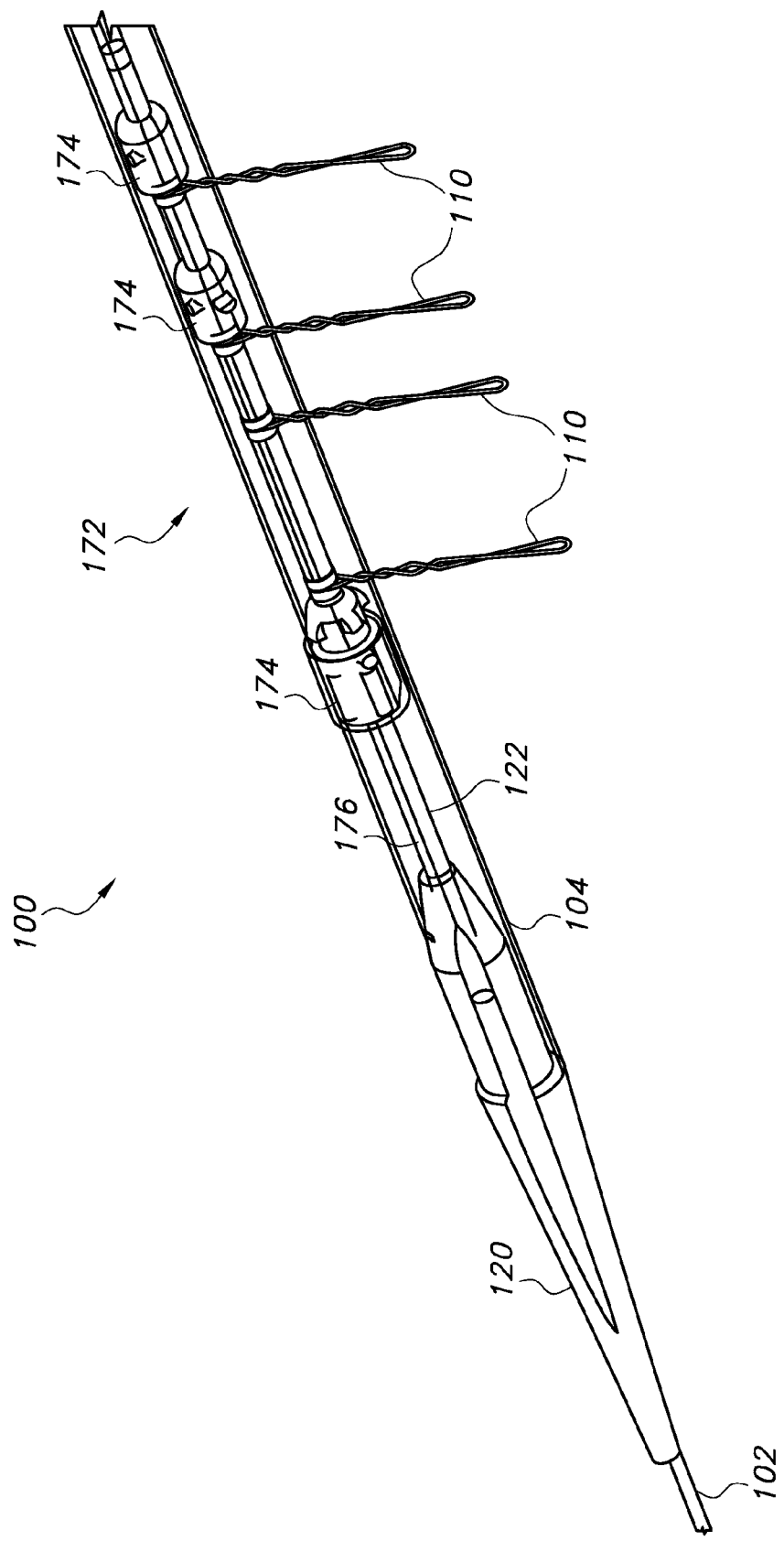
FIG. 8 is a partial perspective and partial cutaway view of the distal portion of the endovascular delivery system of the present invention.

FIG. 7 is a side elevational and partial cutaway view of the distal portion 172 of the endovascular delivery system 100 of the present invention, and FIG. 8 is a partial perspective and partial cutaway view of the distal portion 172 of the endovascular delivery system 100 of the present invention. The distal portion 172 of the endovascular delivery system 100 includes a prosthesis/stent holder 174 disposed upon a prosthesis/stent holder guidewire 176. The holder 174 is useful releasably securing the endovascular prosthesis 106 (not shown) within the delivery system 100. The holder 174 inhibits or substantially inhibits undesirable longitudinal and/or circumferential movement of the endovascular prostheses 106 during delivery stages of the delivery system 100. Belts 110 serve to restrain the endovascular prosthesis 106 in a radially constrained stage until desired release of the endovascular prosthesis 106.

Figure 9:
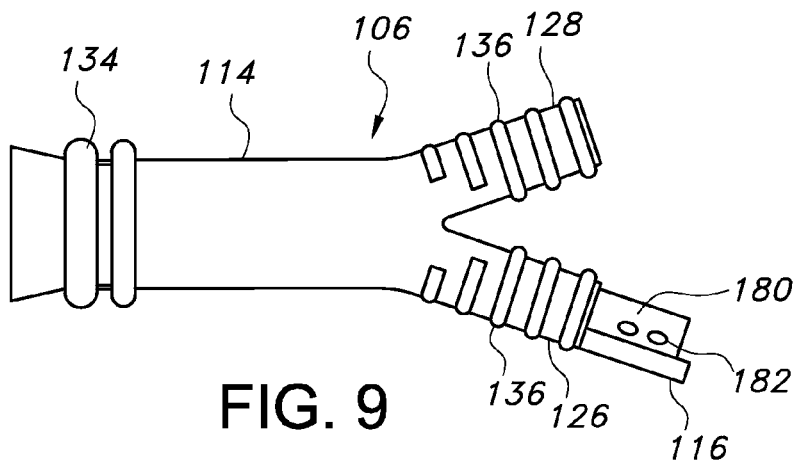
FIG. 9 is an elevational view of the prosthesis of the present invention having a flap at the ipsilateral leg.

FIG. 9 is an elevational view of the prosthesis 106 of the present invention having a flap 180 at the ipsilateral leg 126. The flap 180 may be made from any of the above-described graft materials. In some embodiments, the flap 180 is made from polytetrafluoroethylene. The flap 180 may include two holes 182. The width of the flap may be from about 10% to about 90% of the circumference of the ipsilateral leg 126. In some embodiments, the width is from about 30% to about 60%; in other embodiments, from about 45% to about 55%. The flap 182 may contain two holes 182 as shown in FIG. 9, one hole, or more than two holes. A hole diameter of about 0.06 inches is useful, although hole diameters may be higher or lower. In the case of more than one hole, the hole diameters may vary between or among holes.

Figure 10:
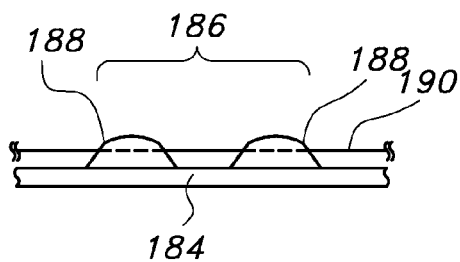
FIG. 10 is a partial elevational view of a distal stop on a delivery guidewire for restraining the ipsilateral leg of the prosthesis during certain delivery stages of the prosthesis.
Figure 11:
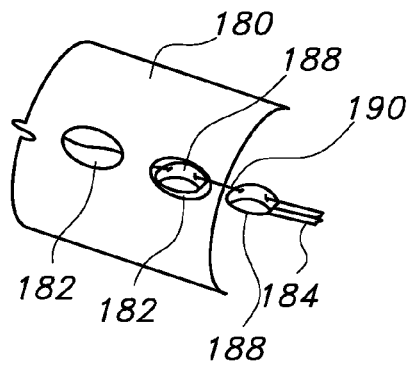
FIG. 11 is an exploded and partial cut-away view of the distal stop initially engaging the ipsilateral leg flap.
Figure 12:
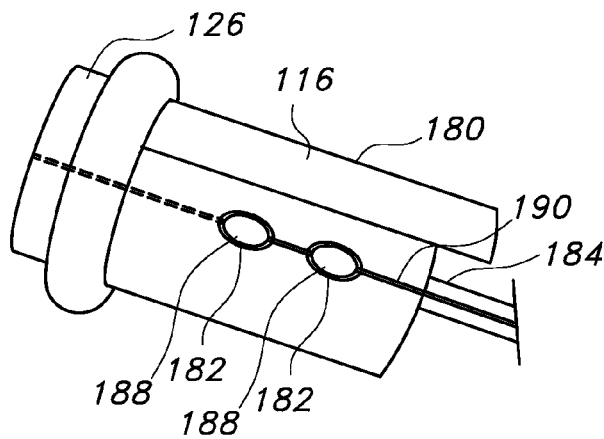
FIG. 12 is an exploded and partial cut-away view of the distal stop engaging the ipsilateral leg flap.

FIG. 10 is a partial elevational view of one embodiment including a distal stop 186 on a delivery guidewire 184 for restraining the ipsilateral leg 126 of the prosthesis 106 during certain delivery stages of the prosthesis 106. The distal stop 186 includes two raised projections 188 securably attached to a guidewire 184. A release wire 190 is slidably disposed within the projections 188. As depicted in FIGS. 11 and 12, the distal stop 186 is useful for releasably securing the ipsilateral leg 126, in particular the flap 180, to the distal stop 186 and the guidewire 184. The raised projections 188 may be secured or disposed within one or both of the flap holes 182. The release wire 190 is thus releasably inter-looped or interlaced within or to the flap 180.

FIG. 13 is a schematic depiction of the ends of the contralateral and ipsilateral graft legs 128, 126 of the prosthesis 106 having a contralateral tether 192. The contralateral tether 192 has a contralateral end 196 and an opposed ipsilateral end 198. The contralateral end 196 is securably disposed to the end of the contralateral leg 128. The contralateral tether 192 may also be made from any of the above-described graft materials. In some embodiments, the contralateral tether 192 is made from polytetrafluoroethylene. As depicted in FIGS. 13 and 14, the release wire 190 releasably engages a portion of the tether 192. In some embodiments, the release wire 190 is slidably disposed through a hole 194 near the ipsilateral end 198 of the tether 192 as depicted in FIG. 13. When the release wire 190 is engaged with the tether 192, undesirably longitudinal movement, such as bunching, of the contralateral leg 128 is mitigated or even prevented as the contralateral leg 128 is ultimately and relatively restrained by the release wire and the ipsilateral leg 126 is relatively restrained by the distal stop 186 and the release wire 190. The contralateral tether 192 may also mitigate or prevent undesirable rotation of the contralateral leg 128 with respect to the ipsilateral leg 126 when the tether 192 is so engaged with the release wire 190.

In some embodiments, the tether 192 can withstand aggressive cannulation without disconnecting from the contralateral leg 128. For example, the tether 192 may have a tensile strength greater than 0.5 pounds-force per square inch (psi), which is an approximate maximum force which may be applied clinically. The tether 192 may have a tensile strength of about 2.0 psi. Such a tensile strength is non-limiting. Use of the contralateral tether 192 also allows filling of the inflatable graft 114 without impingement of the fill tube 116 or the network of channels 136. In the case of narrow distal aortic necks or in acute aortoiliac angles, a "ballerina" type crossover configuration (also referred to as a "barber pole: configuration) of the ipsilateral and contralateral graft legs may be used by a practitioner. In such a "ballerina" type crossover configuration the two iliac graft limbs may cross each other one or more times distal to the aortic body but before entering the iliac arteries of a patient treated with a bifurcated graft. Such a "ballerina" type crossover configuration may be achieved even with the use of the tether 192 with the inflatable graft 114 of the present invention. Moreover, use of the tether 192 prevents undesirably leg 126, 128 flipping during positioning of the inflatable graft 114.

The tether 192 width may be from about 2 to 5 mm, and its length may be from about 5 to 20 mm. These dimensions are non-limiting dimensions, and other suitable dimensions may be used. For example, in some embodiments (not shown), the contralateral tether 192 may have an ipsilateral end 198 that is not configured for engagement with a release wire 190 but rather is configured to run through the inner tubular member 150 and terminate at the proximal handle assembly 170 of the delivery system and releasably secured to a component thereof, such as an additional knob on handle assembly 170. A longer contralateral tether 192 of such a configuration may be manipulated by the physician-user in the same manner to mitigate or prevent undesirable movement or rotation of one or both legs 126, 128 during positioning of the inflatable graft 114 as described herein. This may provide beneficial positioning control or manipulation of the legs 126, 128, as opposed to must mitigating or preventing undesirable movement. Such a longer tether 192 would not necessary have to come all the way out of the handle 170, but alternatively could be engaged by a control wire or other control mechanism terminating at or near the handle 170.

Figure 17:
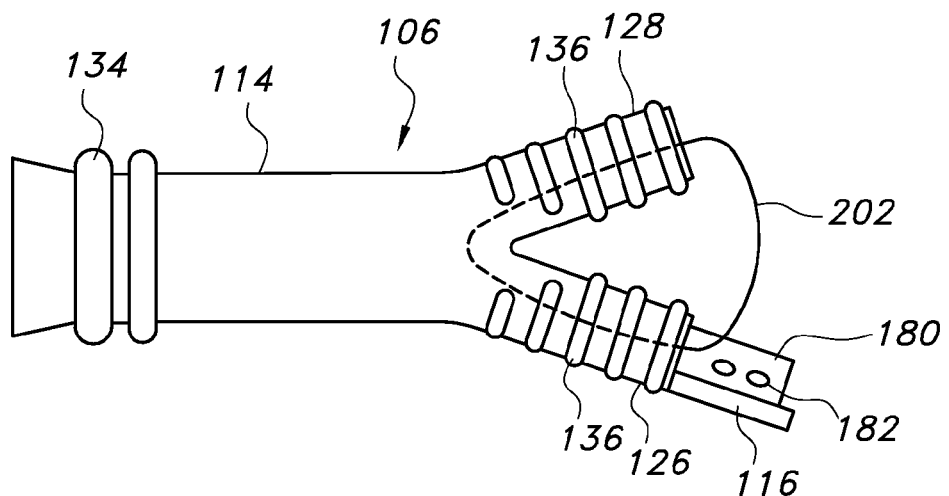
Figure 18:
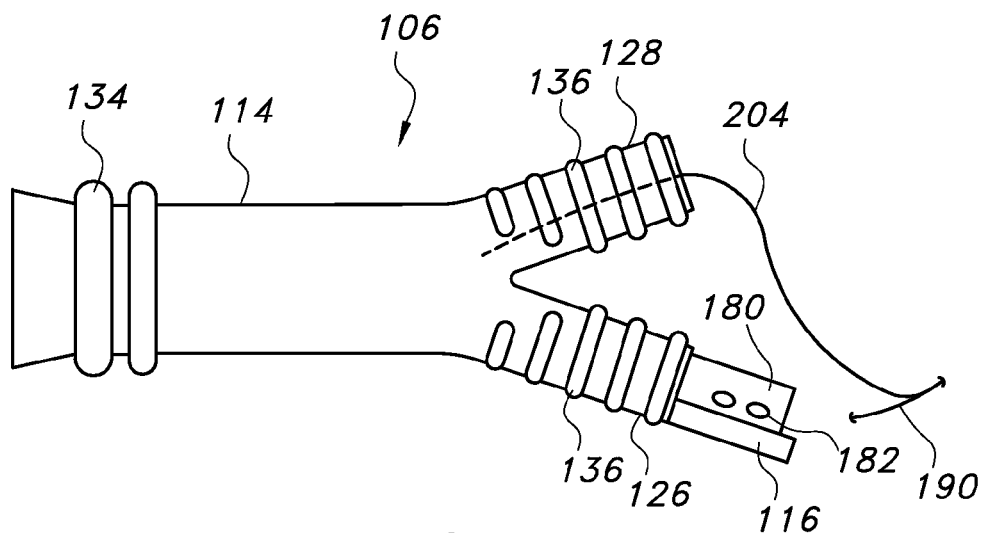

The present invention, however, is not limited to the use of the tether 192 to restrain the contralateral leg 128 during deployment, and other suitably arrangements may be used. For example, as depicted in FIGS. 15 and 16, the release wire 190 may be looped through a hole 200 in the contralateral leg 128. As depicted in FIG. 17, a loop 202 of polymeric material, such a polytetrafluoroethylene, may be disposed between the contralateral leg 128 and the ipsilateral leg 126. The loop 202 may be withdrawn via a release wire (not shown) which may have only one end (not shown) the loop secured thereto. Moreover, as depicted in FIG. 18, a relatively stiffer polymeric member 204, such as a polyamide tube of thread, may be used to restrain movement of the contralateral leg 128 relative to the ipsilateral leg 126. Such a polymeric member 204 may be secured to the release wire 190 or to another release wire within the delivery system 100. These examples of non-tethering restrains are not limiting and other restraining arrangements may be suitably be used.

Figure 19:
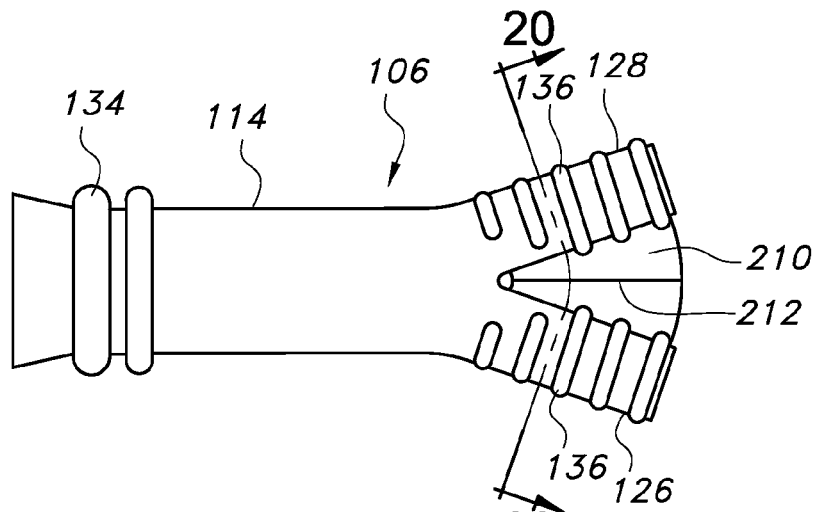
FIGS. 19 through 21 depict further alternate embodiments of the present invention for restraining the contralateral leg.
Figure 20:
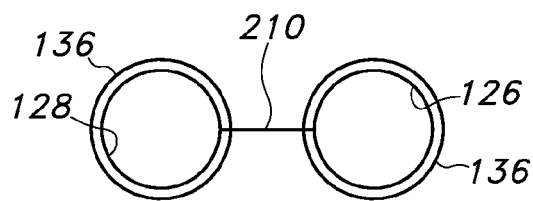
Figure 21:
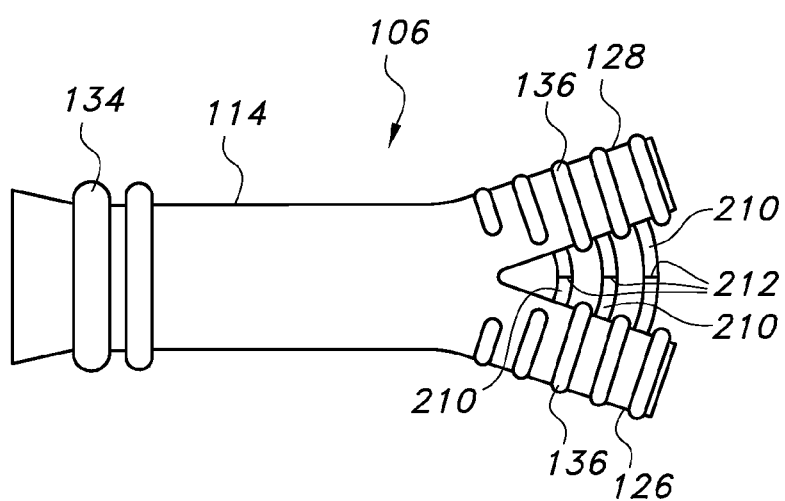

The present invention, however, is not limited to the use of the above-described tether 192, the above-described release wire 190 and/or the above-described a loop 202 to restrain the contralateral leg 128 during deployment, and other suitably arrangements may be used. For example, as depicted in FIGS. 19 through 21, a web 210 may be disposed between the contralateral leg 128 and the ipsilateral leg 126. The web 210 may be fabricated from any useful biocompatible materials, including biocompatible materials used to form endovascular prosthesis 106 or sections of the endovascular prosthesis 106, such as the contralateral leg 128 and/or the ipsilateral leg 126.

As depicted in FIG. 19, the web 210 may be substantially disposed between the contralateral leg 128 and the ipsilateral leg 126 to so constrain relative movement of the legs 128, 126 during initial stages of deployment of the endovascular prosthesis 106. The web 210 may be cut or otherwise separated into portions during delivery by the practitioner so as to facilitate proper placement of the contralateral leg 128 and the ipsilateral leg 126. During delivery of the endovascular prosthesis 106. Such portions may be removed by the practitioner or may remain within the aortic aneurysm 20. Furthermore, the web 210 may contain a weakened portion or tear-line 212. The tear-line 212 may be configured to allow separation of one portion of the web 210 from another portion of the web 210 upon application of a displacement force (not shown) by the practitioner to separate of properly position the contralateral leg 128 and the ipsilateral leg 126 within the aortic aneurysm 20 or proximal to the aortic aneurysm 20, for example near or within the iliac arteries 14, 16. As such, the web 210 may be secured to the contralateral leg 128 and the ipsilateral leg 126, including releasably secured to the contralateral leg 128 and the ipsilateral leg 126.

FIG. 20 is a cross-section view of the contralateral leg 128, the ipsilateral leg 126 and the web 210 taken along the 20-20 axis of FIG. 19. As depicted in FIG. 20, the web 210 is a sheet of material inter-connecting or inter-engaging the contralateral leg 128 and the ipsilateral leg 126. While the web 210 is as a planar sheet in FIGS. 19 and 20, the present invention is not so limited. The web 210 may be non-planar in shape (not shown), for example having slag or folded over sections to permit a degree of movement between the contralateral leg 128 and the ipsilateral leg 126. Furthermore, the web 210 is not limited to being a sheet of material. For example, the web 210 may itself be perforated, such as but not limited to a screen configuration, where the web 210 may have interstitial openings (not shown) or openable interstitial apertures (not shown) to permit greater flexibility over a planar sheet of material. Moreover, as depicted in FIG. 21, a plurality of webs 210 may suitable be used to inter-connecting or inter-engaging the contralateral leg 128 and the ipsilateral leg 126.

The web 210 may be shaped, configured or constructed to allow more leg independent mobility at the distal portions of the legs 126, 128 as compared to proximal leg portions near the bifurcation portion of the graft or prosthesis 106. For example, the web 210 may have a curved and/or indented distal edge(s) or portion(s) near the distal portions of the legs 126, 128, where such curved and/or indented distal web edge(s) or portion(s) allows or permits the legs 126, 128 more relative independent movement as compared to a regular-shaped or triangular-shaped web 210 as depicted in FIG. 19. Such increased leg independent mobility at the distal portions of the legs 126, 128 may also be achieved by any suitable means. On additional, non-limiting example includes varying the thickness of the web 210 to achieve such increased leg independent mobility at the distal portions of the legs 126, 128. For example, portions of the web 210 near the distal portions of the legs 126, 128 could have reduced thickness, i.e., thinner, as compared to portions of the web 201 near the bifurcation of the graft or prosthesis 106. Further, the materials of construction of the web 210 may vary such that web portions near the distal portions of the legs 126, 128 include materials having greater modulus of flexibility and/or elasticity as compared materials portions of the web 201 near the bifurcation of the graft or prosthesis 106.

The following embodiments or aspects of the invention may be combined in any fashion and combination and be within the scope of the present invention, as follows:

Embodiment 1

An endovascular delivery system, comprising:
a bifurcated and inflatable prosthesis comprising:
    a main tubular body having an open end and opposed ipsilateral and contralateral legs defining a graft wall therein between, said ipsilateral and contralateral legs having open ends, and said main tubular body and said ipsilateral and contralateral legs having inflatable channels;
    said ipsilateral leg comprising an ipsilateral tab extending from the open end of said ipsilateral leg, said tab comprising at least two holes;
an elongate guidewire having at least two outwardly projecting members, said outwardly projecting members being sized to at least partially fit within the at least one of said at least two holes of said ipsilateral tab;
a release wire slidable disposed within the at least two outwardly projecting members of the elongate guidewire and within one of the at least two holes of said ipsilateral tab; and
a tether having opposed contralateral and ipsilateral ends, said contralateral end of the tether being securably disposed at said open end of said contralateral leg, said ipsilateral end of the tether having a hole, said release wire being slidably disposed through the hole of the tether to so engage the tether;
wherein withdrawal of the release wire releases the ipsilateral tab and the tether from the elongate guidewire.

Embodiment 2

The endovascular delivery system of embodiment 1, wherein, when said release wire engages said tether, the open end of the contralateral leg is proximally disposed and restrained towards the open end of the ipsilateral leg.

Embodiment 3

The endovascular delivery system of embodiment 2, wherein the contralateral leg is restricted from significant longitudinal movement so as to prevent bunching up of the contralateral leg.

Embodiment 4

The endovascular delivery system of embodiment 2, wherein the contralateral leg is restricted from significant rotational movement so as to prevent misalignment within a bodily lumen.

Embodiment 5

The endovascular delivery system of embodiment 1, wherein said elongate guidewire is extendable through the ipsilateral leg and through the main tubular body.

Embodiment 6

The endovascular delivery system of embodiment 1, further comprising:
an elongate outer tubular sheath having an open lumen and opposed proximal and distal ends with a medial portion therein between, the proximal end of the outer tubular sheath securably disposed to a first handle;
an elongate inner tubular member having a tubular wall with an open lumen and opposed proximal and distal ends with a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle;
said elongate guidewire slidably disposed within the inner tubular member;
the distal end of the outer tubular sheath being slidably disposed past and beyond the distal end of the inner tubular member to define a prosthesis delivery state and slidably retractable to the medial portion of the inner tubular member to define a prosthesis unsheathed state.

Embodiment 7

The endovascular delivery system of embodiment 1, wherein the prosthesis comprises non-textile polymeric material.

Embodiment 8

The endovascular delivery system of embodiment 1, wherein the non-textile polymeric material of the prosthesis comprises extruded polytetrafluoroethylene.

Embodiment 9

The endovascular delivery system of embodiment 8, wherein said extruded polytetrafluoroethylene is non-porous polytetrafluoroethylene.

Embodiment 10

The endovascular delivery system of embodiment 1, wherein the prosthesis further comprises a metallic expandable member securably disposed at or near the open end of the main tubular body of said prosthesis.

Embodiment 11

A method for delivering a bifurcated prosthesis, comprising:
providing a bifurcated and inflatable prosthesis comprising:
    a main tubular body having an open end and opposed ipsilateral and contralateral legs defining a graft wall therein between, said ipsilateral and contralateral legs having open ends, and said main tubular body and said ipsilateral and contralateral legs having inflatable channels;

said ipsilateral leg comprising an ipsilateral tab extending from the open end of said ipsilateral leg, said tab comprising at least two holes;

providing an elongate guidewire having at least two outwardly projecting members, said outwardly projecting members being sized to at least partially fit within at least one of said at least two holes of said ipsilateral tab;

providing a release wire slidable disposed within the at least two outwardly projecting members of the elongate guidewire and within the at least two holes of said ipsilateral tab;

providing a tether having opposed contralateral and ipsilateral ends, said contralateral end of the tether being securably disposed at said open end of said contralateral leg, said ipsilateral end of the tether having a hole, said release wire being slidably disposed through the hole of the tether to so engage the tether; and withdrawing the release wire to release the ipsilateral tab and the tether from the elongate guidewire.

Embodiment 12

The method of embodiment 11, wherein, when said release wire engages said tether, the open end of the contralateral leg is proximally disposed and restrained towards the open end of the ipsilateral leg.

Embodiment 13

The method of embodiment 12, wherein the contralateral leg is restricted from significant longitudinal movement so as to prevent bunching up of the contralateral leg.

Embodiment 14

The method of embodiment 12, wherein the contralateral leg is restricted from significant rotational movement so as to prevent misalignment within a bodily lumen.

Embodiment 15

An endovascular prosthesis, comprising:
a bifurcated and inflatable prosthesis comprising:
a main tubular body having an open end and opposed ipsilateral and contralateral legs defining a graft wall therein between, said ipsilateral and contralateral legs having open ends, and said main tubular body and said ipsilateral and contralateral legs having inflatable channels; and
a web of biocompatible material disposed between the contralateral leg and the ipsilateral leg and secured to the contralateral leg and the ipsilateral leg;
wherein the contralateral leg is restricted from significant longitudinal movement so as to prevent bunching up of the contralateral leg during delivery of the endovascular prosthesis.

Embodiment 16

The endovascular prosthesis of embodiment 15, wherein the contralateral leg is restricted from significant rotational movement so as to prevent misalignment within a bodily lumen.

Embodiment 17

The endovascular prosthesis of embodiment 15, wherein the web is releasably secured to the contralateral leg and the ipsilateral leg.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. An endovascular delivery system, comprising:
a bifurcated prosthesis comprising:
a main tubular body having an open end and opposed ipsilateral and contralateral legs defining a graft wall therein between, said ipsilateral and contralateral legs having open ends;
said ipsilateral leg comprising an ipsilateral tab extending from the open end of said ipsilateral leg, said tab comprising at least two holes;
an elongate guidewire having at least two outwardly projecting members, said outwardly projecting members being sized to at least partially fit within the at least one of said at least two holes of said ipsilateral tab;
a release wire slidable disposed within the at least two outwardly projecting members of the elongate guidewire and within one of the at least two holes of said ipsilateral tab; and
a tether having opposed contralateral and ipsilateral ends, said contralateral end of the tether being securably disposed at said open end of said contralateral leg, said ipsilateral end of the tether having a hole, said release wire being slidably disposed through the hole of the tether to so engage the tether;
wherein withdrawal of the release wire releases the ipsilateral tab and the tether from the elongate guidewire.

2. The endovascular delivery system of claim 1, wherein, when said release wire engages said tether, the open end of the contralateral leg is proximally disposed and restrained towards the open end of the ipsilateral leg.

3. The endovascular delivery system of claim 2, wherein the contralateral leg is restricted from significant longitudinal movement so as to prevent bunching up of the contralateral leg.

4. The endovascular delivery system of claim 2, wherein the contralateral leg is restricted from significant rotational movement so as to prevent misalignment within a bodily lumen.

5. The endovascular delivery system of claim 1, wherein said elongate guidewire is extendable through the ipsilateral leg and through the main tubular body.

6. The endovascular delivery system of claim 1, further comprising:
an elongate outer tubular sheath having an open lumen and opposed proximal and distal ends with a medial portion therein between, the proximal end of the outer tubular sheath securably disposed to a first handle;
an elongate inner tubular member having a tubular wall with an open lumen and opposed proximal and distal ends with a medial portion therein between, the inner tubular member having a longitudinal length greater than a longitudinal length of the outer tubular sheath, the inner tubular member being slidably disposed within the open lumen of the outer tubular sheath, the proximal end of the inner tubular member securably disposed to a second handle;

said elongate guidewire slidably disposed within the inner tubular member;

the distal end of the outer tubular sheath being slidably disposed past and beyond the distal end of the inner tubular member to define a prosthesis delivery state and slidably retractable to the medial portion of the inner tubular member to define a prosthesis unsheathed state.

7. The endovascular delivery system of claim 1, wherein the prosthesis comprises non-textile polymeric material.

8. The endovascular delivery system of claim 1, wherein the non-textile polymeric material of the prosthesis comprises extruded polytetrafluoroethylene.

9. The endovascular delivery system of claim 8, wherein said extruded polytetrafluoroethylene is non-porous polytetrafluoroethylene.

10. The endovascular delivery system of claim 1, wherein the prosthesis further comprises a metallic expandable member securably disposed at or near the open end of the main tubular body of said prosthesis.

11. The endovascular delivery system of claim 1, wherein the bifurcated prosthesis further comprises:

a web of biocompatible material disposed between the contralateral leg and the ipsilateral leg and secured to the contralateral leg and the ipsilateral leg;

wherein the contralateral leg is restricted from significant longitudinal movement so as to prevent bunching up of the contralateral leg during delivery of the endovascular prosthesis.

12. The endovascular delivery system of claim 11, wherein the contralateral leg is restricted from significant rotational movement so as to prevent misalignment within a bodily lumen.

13. The endovascular delivery system of claim 11, wherein the web is releasably secured to the contralateral leg and the ipsilateral leg.

14. The endovascular delivery system of claim 1, wherein the bifurcated prosthesis is a bifurcated and inflatable prosthesis.

15. The endovascular delivery system of claim 14, wherein said main tubular body and said ipsilateral and contralateral legs comprise inflatable channels.

16. A method for delivering a bifurcated prosthesis, comprising:

providing a bifurcated prosthesis comprising:

a main tubular body having an open end and opposed ipsilateral and contralateral legs defining a graft wall therein between, said ipsilateral and contralateral legs having open ends;

said ipsilateral leg comprising an ipsilateral tab extending from the open end of said ipsilateral leg, said tab comprising at least two holes;

providing an elongate guidewire having at least two outwardly projecting members, said outwardly projecting members being sized to at least partially fit within at least one of said at least two holes of said ipsilateral tab;

providing a release wire slidable disposed within the at least two outwardly projecting members of the elongate guidewire and within the at least two holes of said ipsilateral tab;

providing a tether having opposed contralateral and ipsilateral ends, said contralateral end of the tether being securably disposed at said open end of said contralateral leg, said ipsilateral end of the tether having a hole, said release wire being slidably disposed through the hole of the tether to so engage the tether; and withdrawing the release wire to release the ipsilateral tab and the tether from the elongate guidewire.

17. The method of claim 16, wherein, when said release wire engages said tether, the open end of the contralateral leg is proximally disposed and restrained towards the open end of the ipsilateral leg.

18. The method of claim 17, wherein the contralateral leg is restricted from significant longitudinal movement so as to prevent bunching up of the contralateral leg.

19. The method of claim 17, wherein the contralateral leg is restricted from significant rotational movement so as to prevent misalignment within a bodily lumen.

20. The method of claim 16, wherein the bifurcated prosthesis is a bifurcated and inflatable prosthesis.

21. The method of claim 20, wherein the bifurcated prosthesis is a bifurcated and inflatable prosthesis.

* * * * *